United States Patent
Akiyama et al.

(10) Patent No.: US 6,628,492 B2
(45) Date of Patent: Sep. 30, 2003

(54) DISARM CIRCUIT USING SEMICONDUCTOR SWITCH DEVICE

(75) Inventors: Naoto Akiyama, Tokyo (JP); Masahiko Inomata, Tokyo (JP); Ikuhiro Tsumura, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 291 days.

(21) Appl. No.: 09/854,664

(22) Filed: May 15, 2001

(65) Prior Publication Data

US 2001/0043451 A1 Nov. 22, 2001

(30) Foreign Application Priority Data

May 16, 2000 (JP) .................................. P. 2000-143991

(51) Int. Cl.[7] .......................... H02H 3/00; H01T 23/00
(52) U.S. Cl. ...................................... 361/93.9; 361/232
(58) Field of Search .................. 361/230, 232, 361/235, 18, 35, 38, 57, 93.1, 93.5, 93.7, 93.9, 101; 323/908

(56) References Cited

U.S. PATENT DOCUMENTS

| | | | | |
|---|---|---|---|---|
| 5,023,542 A | * | 6/1991 | Banura | 323/284 |
| 5,698,973 A | * | 12/1997 | Goerke et al. | 323/901 |
| 6,104,584 A | * | 8/2000 | Liu | 361/18 |
| 6,320,365 B1 | * | 11/2001 | D'Angelo | 323/316 |
| 6,498,466 B1 | * | 12/2002 | Edwards | 323/282 |

* cited by examiner

*Primary Examiner*—Matthew V. Nguyen
(74) *Attorney, Agent, or Firm*—Sughrue Mion, PLLC (57) ABSTRACT

The invention has an object of providing a disarm circuit using a semiconductor switch device that can secure the safety of an electrotherapy apparatus by disarming even if the control of the semiconductor switch is disabled because of some cause. Therefore, the disarm circuit is provided with a transformer, its primary side area, its secondary side area, a resistor for disarming and the semiconductor switch device. The secondary side area is characterized in that a resistor for limiting excessive current for automatically turning on the semiconductor switch device by stored electric energy is connected between a positive terminal of an electric energy storage section and the gate of the semiconductor switch device.

12 Claims, 7 Drawing Sheets

DISARM CIRCUIT USING SEMICONDUCTOR SWITCH DEVICE

BACKGROUND OF THE INVENTION

1. Field of the Invention

The present invention relates to a disarm circuit using a semiconductor switch device, particularly relates to a disarm circuit using a semiconductor switch device used for an electrotherapy apparatus for defibrillation.

2. Related Art

An arrhythmia, particularly ventricular fibrillation in the heart of a patient having cardiac disease suddenly kills the patient. To terminate the fibrillation, an electrotherapy apparatus for terminating the fibrillation by applying a shock by an electric pulse to the heart of the patient (also called a defibrillator) is generally used.

Such an electrotherapy apparatus is provided with an electric energy storage section that generates a high-voltage electric pulse such as a capacitor. A method of forcedly discharging high-voltage electric energy left inside the electrotherapy apparatus (the electric energy storage section) after the electrotherapy apparatus is used to secure safety has been considered.

For one method, there is a method of providing a disarm circuit using a semiconductor switch device.

Referring to the drawings, a method of discharging by a disarm circuit using a semiconductor switch in a conventional type electrotherapy apparatus will be described below.

Figure 7:
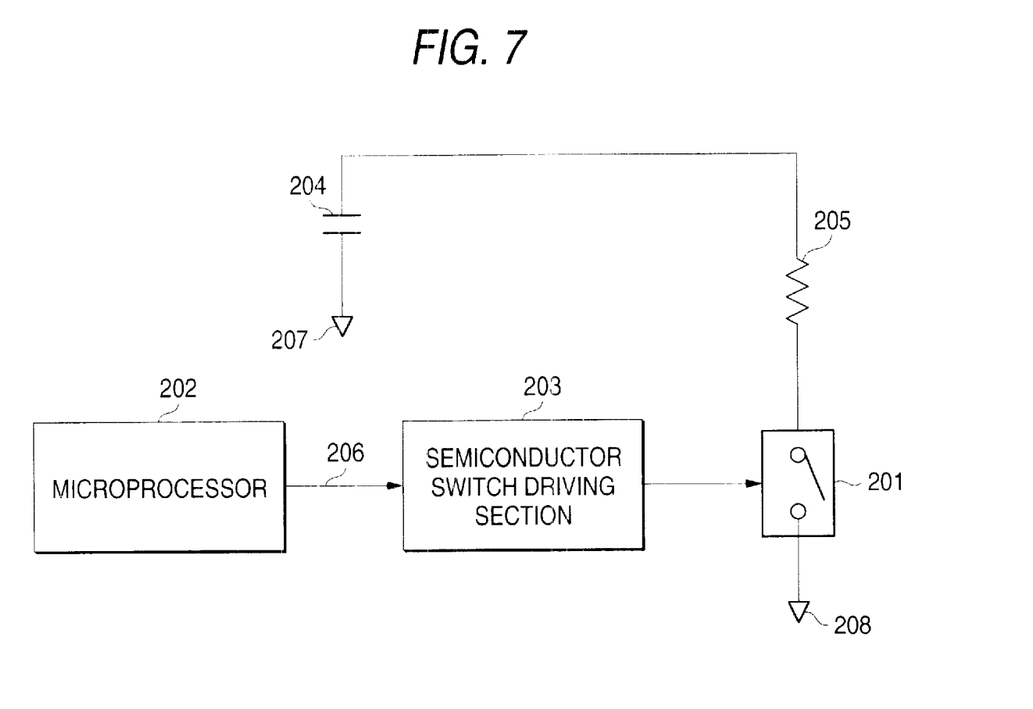
FIG. 7 is a schematic drawing for explaining a disarming method using a semiconductor switch in a conventional type electrotherapy apparatus.

FIG. 7 is a schematic drawing for explaining a method of disarming by the disarm circuit using the semiconductor switch in the conventional type electrotherapy apparatus.

As shown in FIG. 7, the on-off control of the semiconductor switch 201 is performed by a semiconductor switch driving section 203 controlled according to a control signal 206 from a microprocessor 202.

A resistor for disarming 205 is inserted between an electric energy storage section (a capacitor) 204 for storing high-voltage electric energy and the semiconductor switch 201, current flows to a ground terminal 208 via the resistor for disarming 205 by turning on the semiconductor switch 201 and electric energy is disarmed.

However, the method of discharging by the disarm circuit using the semiconductor switch in the conventional type electrotherapy apparatus has the following problems.

The semiconductor switch 201 is controlled by the semiconductor switch driving section 203 controlled according to a control signal from the microprocessor 202 and therefore, when the control of the semiconductor switch 201 is disabled due to the unexpected cutoff of power supply by the disconnection of a battery and others and some failure of the apparatus such as the single fault of a control circuit, the semiconductor switch 201 is turned off and energy stored in the electric energy storage section 204 is not disarmed.

Therefore, the method of disarming by the disarm circuit using the semiconductor switch in the conventional type electrotherapy apparatus has a problem of safety that in case the control of the switch is disabled because of some cause, high-voltage electric energy remains in the circuit undischarged and when the electrotherapy apparatus is operated or repaired, an operator or a repairman may get electric shock.

SUMMARY OF THE INVENTION

The invention is made to solve the problem of the related art and the object is to provide a disarm circuit using a semiconductor switch device wherein the safety of an electrotherapy apparatus can be secured by disarming even if the control of a semiconductor switch is disabled because of some cause.

To achieve the object, a disarm circuit using a semiconductor switch device according to a first aspect is based upon A disarm circuit comprising a semiconductor switch device discharging electric energy stored in an electric energy storage section by turning on the semiconductor switch device according to a control signal from a control circuit via a first resistor for disarming provided between one terminal of the electric energy storage section and a first terminal of the semiconductor switch device; and a second resistor for limiting current which flows from one terminal of the electric energy storage section and for transmitting the current to a control terminal of the semiconductor switch device, the second resistor being provided between one terminal of the electric energy storage section and the control terminal of the semiconductor switch device, electric energy stored in the electric energy storage section automatically turns on the semiconductor switch device and is discharged via the resistor for disarming in case the control of the semiconductor switch is disabled because of some cause when the electric energy storage section is disarmed.

As a disarm circuit using a semiconductor switch device according to a second aspect is formed so that a transformer is at least provided, a primary side area controlling current on the primary side of the transformer according to a control signal for controlling the semiconductor switch device, the primary area being provided on the primary side of the transformer;

a secondary side area directly driving the semiconductor switch device, the secondary side area being provided on the secondary side of the transformer, wherein the primary side area receives a control signal, transmits power for controlling the semiconductor switch device to the secondary side area and inhibits back electromotive force caused when current that flows on a primary winding of the transformer is cut off, back electromotive force caused when current flowing in the transformer is cut off is inhibited.

As the secondary side area in a disarm circuit using a semiconductor switch device according to a third aspect is formed so that the secondary side area receives power supplied from the primary side area, transmits power for controlling the semiconductor switch device to the semiconductor switch and cuts off voltage caused by back electromotive force caused when current that flows on a primary winding of the transformer is cut off so that impedance is lower, compared with the second resistor, the control according to a control signal of the semiconductor switch device is also preceded in a state in which electric energy is stored in an electric energy storage section.

As in the secondary side area in a disarm circuit using a semiconductor switch device according to a fourth aspect, a terminal at one end of a secondary winding of the transformer is connected to a first Zener diode, a second Zener diode such that the same kind terminals of the first and second Zener diodes are connected with the same terminals face to face is connected to a control terminal of the semiconductor switch device via a resistor, a terminal at the other end of the secondary winding of the transformer is connected to a second terminal of the semiconductor switch device and a capacitor is connected between the second Zener diode and the second terminal of the semiconductor switch device, the secondary side area receives power supplied from the primary side area and transmits power for control to the semiconductor switch device.

As in a disarm circuit according to a fifth aspect the plural semiconductor switch devices are provided, the withstand voltage against the application of high voltage has a value acquired by adding the withstand voltage of the switch device of each stage.

As in a disarm circuit according to a sixth aspect, each second resistor for limiting current is connected between one terminal of the electric energy storage section and the control terminal of each semiconductor switch device.

As in a disarm circuit according to a seventh aspect, each third resistor for equalizing the characteristic of each semiconductor switch devices is connected between a first terminal and a second terminal of each semiconductor switch device.

As in a disarm circuit according to an eighth aspect, the second resistor for limiting current for a first stage is connected between one terminal of the electric energy storage section and a control terminal of a semiconductor switch device of the first stage and the second resistor for limiting current for a second or the subsequent stage is connected between a second terminal of the semiconductor switch device and a control terminal of a semiconductor switch device of the next stage.

As a disarm circuit using a semiconductor switch device according to a ninth aspect uses an insulated gate bipolar transistor (IGBT) for the semiconductor switch device, the first terminal functions as the collector, the second terminal functions as the emitter, the control terminal functions as the gate and one terminal of the electric energy storage section is a positive terminal, the device (IGBT) having both the low saturation voltage characteristic of a bipolar transistor and the high-speed switching characteristic of a power MOSFET can be used.

As a disarm circuit using a semiconductor switch device according to a tenth aspect uses a N-channel MOSFET for the semiconductor switch device, the first terminal functions as the drain, the second terminal functions as the source, the control terminal functions as the gate and one terminal of the electric energy storage section is a positive terminal, the N-channel MOSFET can be used for the semiconductor switch device.

As a disarm circuit using a semiconductor switch device according to an eleventh aspect uses a P-channel MOSFET for the semiconductor switch device, the first terminal functions as the drain, the second terminal functions as the source, the control terminal functions as the gate and one terminal of the electric energy storage section is a negative terminal, the P-channel MOSFET can be used for the semiconductor switch device.

As an electrotherapy apparatus according to a twelfth aspect is provided with the disarm circuit using the semiconductor switch device according to any of the first to the eleventh aspects, an external discharging circuit that generates electric pulse and outputs electric energy to a living body (a patient), the electric energy storage section and a charging circuit that charges the electric energy storage section, the safety of the electrotherapy apparatus can be secured by disarming even if the control of the semiconductor switch is disabled because of some cause when the electric energy storage section is disarmed.

DETAILED DESCRIPTION OF THE PREFERRED EMBODIMENTS

Referring to the drawings, embodiments of a disarm circuit using a semiconductor switch device according to the invention will be described in detail below.

Figure 1:
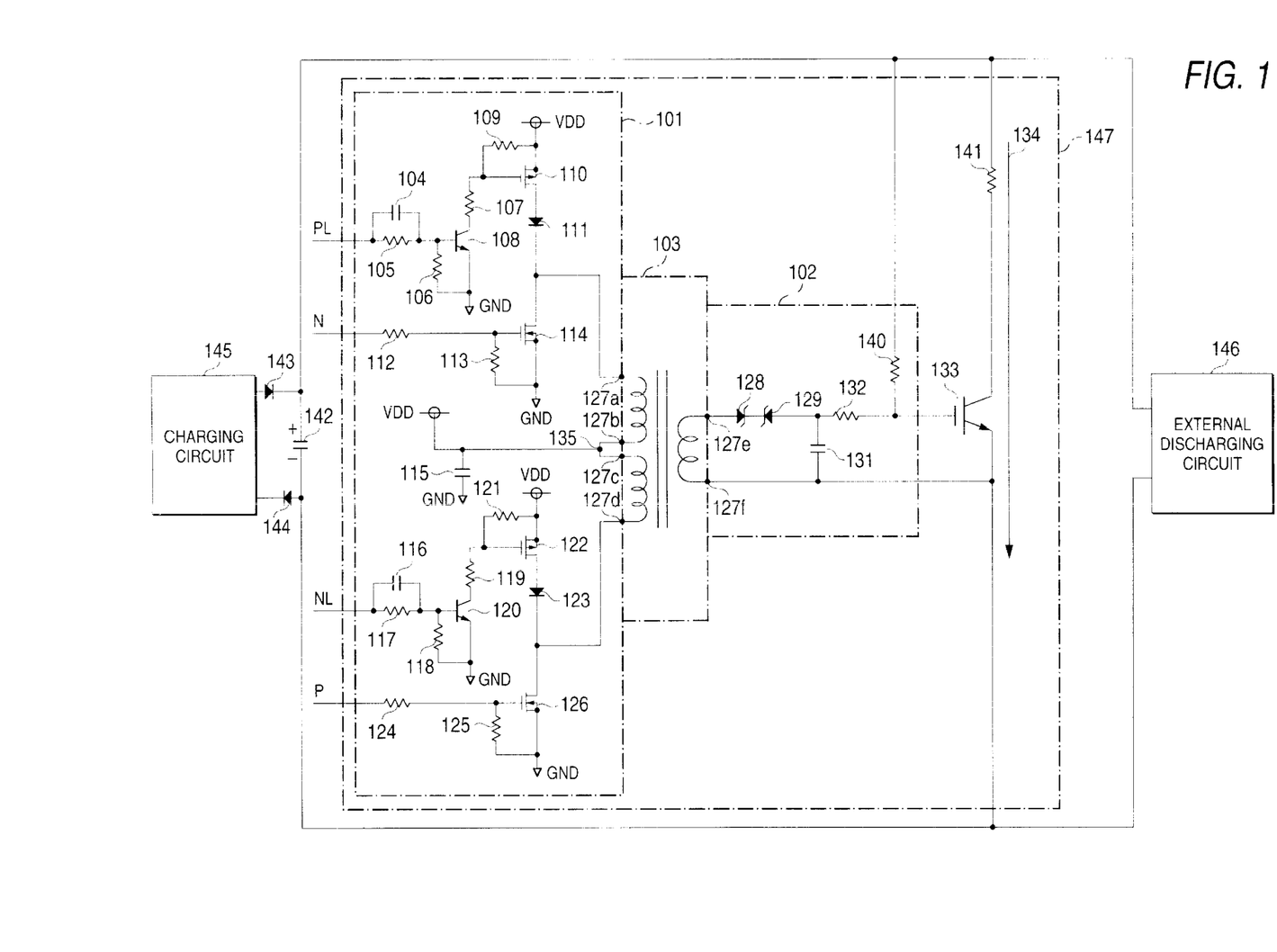
FIG. 1 is a circuit diagram for explaining an embodiment of a disarm circuit using a semiconductor switch device according to the invention and an electrotherapy apparatus.

FIG. 1 is a circuit diagram for explaining the configuration of a discharging circuit of an electrotherapy apparatus including the disarm circuit using the semiconductor switch device according to the invention.

Figure 2:
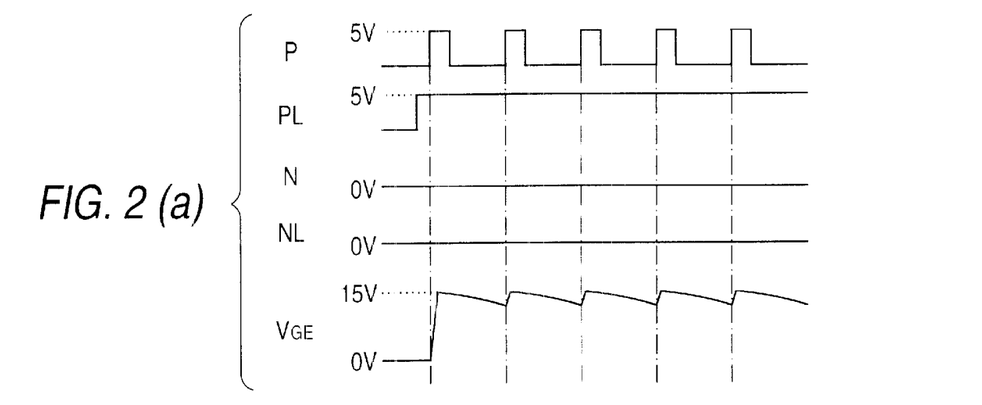
FIGS. 2(a), 2(b), and 2(c) are timing charts in each operation of the disarm circuit using the semiconductor switch device equivalent to this embodiment.

FIGS. 2 are timing charts showing each operation of a disarm circuit using a semiconductor switch device equivalent to this embodiment.

As shown in FIG. 1, the electrotherapy apparatus in this embodiment is provided with an electric energy storage section 142, a circuit for charging it 145, diodes 143 and 144 for preventing current from flowing in a reverse direction to the electric energy storage section 142 while the electric energy storage section 142 is being charged and after the charging is completed, an external discharging circuit 146 for applying an electric pulse to a living body (a patient) and the disarm circuit 147 using the semiconductor switch device for forcedly discharging high-voltage electric energy left inside to secure the safety of the apparatus.

The disarm circuit 147 using the semiconductor switch device equivalent to this embodiment is formed by a transformer 103, its primary side area 101, its secondary side area 102 and a semiconductor switch device 133 and is provided with a resistor for disarming 141 connected between one terminal (a positive terminal) of the electric energy storage section and a first terminal (the collector) of the semiconductor switch device. The secondary side area 102 is characterized in that a resistor for limiting excessive current 140 for automatically turning on the semiconductor switch device 133 by stored electric energy is connected between one terminal (the positive terminal) of the electric energy storage section 142 and the control terminal (the gate) of the semiconductor switch device 133.

Next, the detailed configuration of the disarm circuit 147 will be described.

The primary side area 101 is formed as follows.

A control signal input terminal PL is connected to the base of an NPN bipolar transistor 108 via a resistor 105 and a capacitor 104 respectively connected in parallel, the base and the emitter of the NPN bipolar transistor 108 are connected via a resistor 106 and are connected to a ground terminal GND.

The collector of the NPN bipolar transistor 108 is connected to the gate of a P-channel MOSFET 110 via a resistor 107, the gate and the source of the P-channel MOSFET 110 are connected via a resistor 109 and the source is connected to a DC source VDD.

The drain of the P-channel MOSFET 110 is connected to the anode of a diode 111 and the cathode of the diode 111 is connected to the drain of a N-channel MOSFET 114 and a terminal 127a of a primary winding of the transformer 103.

The gate and the source of the N-channel MOSFET 114 are connected via a resistor 113 and the source is connected to a ground terminal GND. A control signal input terminal N is connected to the gate of the N-channel MOSFET 114 via a resistor 112.

A control signal input terminal NL is connected to the base of an NPN bipolar transistor 120 via a resistor 117 and a capacitor 116 respectively connected in parallel, the base and the emitter of the NPN bipolar transistor 120 are connected via a resistor 118 and the emitter is connected to a ground terminal GND.

The collector of the NPN bipolar transistor 120 is connected to the gate of a P-channel MOSFET 122 via a resistor 119, the gate and the source of the P-channel MOSFET 122 are connected via a resistor 121 and the source is connected to a DC source VDD.

The drain of the P-channel MOSFET 122 is connected to the anode of a diode 123 and the cathode of the diode 123 is connected to the drain of a N-channel MOSFET 126 and a terminal 127d of the primary winding of the transformer 103.

The gate and the source of the N-channel MOSFET 126 are connected via a resistor 125 and the source is connected to a ground terminal GND. A control signal input terminal P is connected to the gate of the N-channel MOSFET 126 via a resistor 124.

Terminals 127b and 127c of the primary winding of the transformer 103 are connected to a center tap 135, further the center tap 135 is connected to a DC source VDD and is connected to a ground terminal GND via a capacitor 115.

The secondary side area 102 is formed as follows.

In the secondary side area 102, a terminal 127e at one end of a secondary winding of the transformer 103 is connected to the anode of a first Zener diode 128, the cathode of the first Zener diode 128 is opposite connected to the cathode of a second Zener diode 129, the anode of the second Zener diode 129 is connected to a control terminal (the gate) of the semiconductor switch device 133 via a resistor 132, a terminal 127f at the other end of the secondary winding is connected to a second terminal (the emitter) of the semiconductor switch device 133 and a capacitor 131 is connected between the anode of the second Zener diode 129 and the second terminal (the emitter) of the semiconductor switch device 133.

Further, the resistor 140 is connected between the positive terminal of the electric energy storage section 142 and the gate of the semiconductor switch device 133.

Next, the function of each area and each circuit will be described.

The primary side area 101 of the disarm circuit receives a control signal and transmits power for controlling the semiconductor switch device 133 to the secondary side area 102 of the disarm circuit. Further, the primary side area 101 inhibits back electromotive force caused when current that flows on the primary winding of the transformer 103 is cut off.

The secondary side area 102 of the disarm circuit receives power supplied from the primary side area 101 of the disarm circuit and transmits power for control to the semiconductor switch device 133.

Further, the secondary side area cuts off voltage caused by back electromotive force caused when current that flows on the primary winding of the transformer 103 is cut off.

The secondary side area receives power supplied from the primary side area 101 and the semiconductor switch device 133 causes or prevents current for switching to flow.

The charging circuit 145 charges the electric energy storage section 142 via the diodes 143 and 144.

The external discharging circuit 146 generates a pulse for defibrillation and outputs it to a living body (a patient).

Further, the function of each circuit component will be described below.

The capacitor 104 speeds up turning on/turning off the bipolar transistor 108.

The resistor 105 limits the base current of the bipolar transistor 108.

The resistor 106 equalizes the base potential of the bipolar transistor 108 to the potential of the emitter.

The resistor 107 limits the collector current of the bipolar transistor 108.

The bipolar transistor 108 executes the on-off control of the P channel MOSFET 110.

The resistor 109 equalizes the gate potential of the P channel MOSFET 110 to the potential of the source.

The P channel MOSFET 110 suppresses voltage caused at the terminal 127a of the primary winding of the transformer 103 by back electromotive force when the N channel MOSFET 126 is turned off.

The diode 111 suppresses voltage caused at the terminal 127a of the primary winding of the transformer 103 by back electromotive force when the N channel MOSFET 126 is turned off so that the voltage at the terminal 127a is at an optimum level. The diode 111 also prevents current in the P channel MOSFET 110 from flowing in a reverse direction by voltage which will be caused by higher voltage than the source voltage at the terminal 127a of the transformer 103 when the N channel MOSFET 126 is turned on The resistor 112 limits the gate current of the N channel MOSFET 114.

The resistor 113 equalizes the gate potential of the N channel MOSFET 114 to the potential of the source.

The N channel MOSFET 114 controls the supply of current to the primary winding of the transformer 103.

The capacitor 115 smoothes source voltage supplied to the transformer 103.

The capacitor 116 contributes to speedup when the bipolar transistor 120 is turned on or turned off.

The resistor 117 limits the base current of the bipolar transistor 120.

The resistor 118 equalizes the base potential of the bipolar transistor 120 to the potential of the collector.

The resistor 119 limits the collector current of the bipolar transistor 120.

The bipolar transistor 120 controls turning on/off the P channel MOSFET 122.

The resistor 121 equalizes the gate potential of the P channel MOSFET 122 to the potential of the source.

The P channel MOSFET 122 suppresses voltage caused at the terminal 127d of the primary winding of the transformer 103 by back electromotive force when the N channel MOSFET 114 is turned off.

The diode 123 suppresses voltage caused at the terminal 127d of the primary winding of the transformer 103 by back electromotive force when the N channel MOSFET 114 is turned off so that the voltage is at an optimum level. The diode 123 also prevents current in a reverse direction from flowing in the P channel MOSFET 122 by voltage which will be caused by higher voltage than the source voltage at the terminal 127*d* of the transformer 103 when the N channel MOSFET 114 is turned on.

The resistor 124 limits the base current of the N channel MOSFET 126.

The resistor 125 equalizes the gate potential of the N channel MOSFET 126 to the potential of the source.

The N channel MOSFET 126 controls the supply of current to the primary winding of the transformer 103.

The transformer 103 insulates between the primary side and the secondary side of the disarm circuit and between the secondary side and the secondary side and transmits power from the primary side to the secondary side.

The Zener diode 128 connects a positive voltage supply path to the semiconductor switch device 133 and cuts off voltage caused between the terminals 127*e* and 127*f* of the secondary winding of the transformer 103 by the back electromotive force of the transformer 103.

The Zener diode 129 connects a negative voltage supply path to the semiconductor switch device 133 and cuts off voltage caused between the terminals 127*e* and 127*f* of the secondary winding of the transformer 103 by the back electromotive force of the transformer 103.

The capacitor 131 keeps the gate voltage of the semiconductor switch device 133.

Further, in case a semiconductor switch device in which plural semiconductor switch devices are connected in series is used though it is not shown, dispersion among the gate capacitance of each semiconductor switch device can be eliminated.

The resistor 132 limits the gate current of the semiconductor switch device 133.

The semiconductor switch device 133 conducts or breaks current for switching 134.

The resistor for limiting excessive current 140 limits current and transmits energy in the electric energy storage section 142 to the gate of the semiconductor switch device 133.

The resistor for disarming 141 consumes energy in the electric energy storage section 142 when the semiconductor switch device 133 is turned on and current for switching 134 is conducted.

The electric energy storage section 142 stores electric energy used for defibrillation.

The diodes 143 and 144 prevent current from flowing in a reverse direction to the charging circuit while the electric energy storage section 142 is being charged and after the charging is completed.

Next, referring to the circuit diagram shown in FIG. 1, the operation of the disarm circuit equivalent to this embodiment will be described.

1. In the case of control according to control signals P, PL, N and NL

The impedance of the circuit (the transformer secondary side area) including 128, 129, 131, 132 and the terminals 127*e* and 127*f* of the secondary winding of the transformer 103 on the side of the resistor 132 when seen from the gate of the semiconductor switch device 133 is lower, compared with that of the resistor for limiting excessive current 140.

Therefore, in a state in which electric energy is stored in the electric energy storage section, the control of the semiconductor switch device according to a control signal is also preceded and the on-off control of the semiconductor switch device 133 according to control signals P, PL, N and NL is enabled.

FIG. 2 (*a*) shows operation for keeping the semiconductor switch conducting (continuously supplying positive voltage).

The operation in the primary side area 101 of the disarm circuit in this operation is as described in the following 1a-1 to 1a-8.

1a-1: Signals N and NL input to the primary side area 101 of the disarm circuit are kept 0 V on the circuit.

1a-2: The level of a control signal PL is changed from 0 V to a level at which the bipolar transistor 108 can be turned on (for example, +5 V).

1a-3: The bipolar transistor 108 becomes a conducting state.

1a-4: The P channel MOSFET 110 becomes a conducting state.

1a-5: After time enough to turn off the bipolar transistor 120 and the P channel MOSFET 122 elapses (for example, in 1 $\mu$ s.) after the level of the control signal NL is made to 0 V in 1a-1, the level of a control signal P is changed from 0 V to a level at which the N channel MOSFET 126 can be turned on (for example, +5 V).

1a-6: The N channel MOSFET 126 becomes a conducting state.

1a-7: Current flows from the terminal 127*c* to the terminal 127*d* in the primary winding of the transformer 103 from the center tap 135 toward the N channel MOSFET 126.

1a-8: Electromotive force V2$p$ which is positive on the side of the terminal 127*e* and is negative on the side of the terminal 127*f* is generated at both ends of each secondary winding of the transformer 103 (refer to the following mathematical expression 1).

$$V2p = V1 \times N2/N1 \tag{1}$$

In the mathematical expression 1, V1 denotes voltage applied between the terminals 127*c* and 127*d* of the transformer 103, N1 denotes the number of turns between the terminals 127*c* and 127*d* and between the terminals 127*a* and 127*b* of the transformer 103 and N2 denotes the number of turns between the terminals 127*e* and 127*f* of the transformer 103.

Next, the operation in the secondary side area 102 of the disarm circuit in this operation is as described in the following 1a-9 to 1a-18.

1a-9: Electromotive force V2$p$ at both ends of each secondary winding increases and exceeds voltage acquired by adding Zener voltage $V_{z29}$ of the Zener diode 129 and the dropout voltage $V_{f28}$ in a forward direction of the Zener diode 128*a* (refer to a mathematical expression 2).

$$V2p > V_{z29} + V_{f28} \tag{2}$$

1a-10: The Zener diode 129 becomes a conducting state.

1a-11: The capacitor 131 is charged (the side of the Zener diode 129 is positive) and the gate capacitance of the semiconductor switch device 133 is charged (the side of the gate is positive) via the resistor 132.

1a-12: The gate voltage $V_{GE}$ of the semiconductor switch device 133 exceeds the gate threshold voltage $V_{GE(TH)}$ (a condition of the mathematical expression 3) and the semiconductor switch device 133 becomes a conducting state.

$$V_{GE33} > V_{GE(TH)} \tag{3}$$

1a-13: After the gate voltage $V_{GE33}$ of the semiconductor switch device 133 becomes at a level (for example, +15 V) enough to keep the switching device conducting (for example, in 2.5 µs.), a control signal P is made to 0 V.

a-14: The N channel MOSFET 126 becomes a non-conducting state.

a-15: Back electromotive force which is positive on the side of the terminal 127d and is negative on the side of the terminal 127a is caused on the primary winding of the transformer 103, however, as the terminal 127a on one side of the winding is connected to a power source via the P channel MOSFET 110 and the diode 111 which are respectively in a conducting state, back electromotive force $V1_{rev}$ caused between the terminals 127a and 127d is inhibited as shown in a mathematical expression 4.

$$V1_{rev}=(V_{d\cdot 10}+V_{fil})\times 2 \qquad (4)$$

$V_{d\cdot 10}$ denotes the dropout voltage of the P channel MOSFET 110 and $V_{fil}$ denotes the dropout voltage in a forward direction of the diode 111.

1a-16: Back electromotive force $V2p_{rev}$ which is positive on the side of the terminal 127f and is negative on the side of the terminal 127e is also caused on the secondary winding by back electromotive force $V1_{rev}$ caused on the primary winding of the transformer 103, however, the level is zener voltage $V_{z28}$ of the Zener diode 128a or less and the circuit on the secondary side becomes a non-conducting state by the Zener diode 128a (refer to a mathematical expression 5).

$$V2P_{rev}=(V1_{rev}\times N2/N1)<V_{z28} \qquad (5)$$

1a-17: The gate voltage $V_{GE33}$ of the semiconductor switch device 133 decreases according to a time constant determined based upon, the capacitor 131 and the resistor 132 and the gate capacitance of the semiconductor switch device 133.

This time constant is determined so that the gate voltage $V_{GE33}$ of the semiconductor switch device 133 can continue to keep the voltage enough to keep the switching device conducting for time enough for magnetic energy stored in the core of the transformer 103 to be consumed.

1a-18: Before the gate voltage $V_{GE33}$ of the semiconductor switch device 133 is the gate threshold voltage $V_{GE<TH}$ or less and after magnetic energy stored in the core of the transformer 103 is consumed, the level of a control signal P is changed from 0 V to a level at which the N channel MOSFET 126 can be turned on (for example, +5 V).

Afterward, 1a-6 to 1a-18 are repeated.

FIG. 2(b) shows operation for keeping the semiconductor switch non-conducting (continuously supplying negative voltage). The operation in the primary side area 101 of the disarm circuit in this operation is as described in the following 1b-1 to 1b-8.

1b-1: Signals P and PL input to the primary side area 101 of the disarm circuit are kept 0 V on the circuit.

1b-2: The level of a control signal NL is changed from 0 V to a level at which the bipolar transistor 120 can be turned on (for example, +5 V).

1b-3: The bipolar transistor 120 becomes a conducting state.

1b-4: The P channel MOSFET 122 becomes a conducting state.

1b-5: After time enough to turn off the bipolar transistor 108 and the P channel MOSFET 110 elapses (for example, in 1 µs.) after the control signal PL is made to 0 V at 1b-5, the level of a control signal N is changed from 0 V to a level at which the N channel MOSFET 114 can be turned on (for example, +5 V).

1b-6: The N channel MOSFET 114 becomes a conducting state.

1b-7: Current flows (from the terminal 127b to the terminal 127a) in the primary winding of the transformer 103 from the center tap toward the N channel MOSFET 114.

b-8: Electromotive force V2n which is positive on the side of the terminal 127f and is negative on the side of the terminal 127e is generated at both ends of each secondary winding of the transformer 103 (refer to a mathematical expression 6).

$$V2n=V1\times N2/N1 \qquad (6)$$

V1 denotes voltage applied between the terminals 127b and 127a of the transformer 103, N1 denotes the number of turns between the terminals 127a and 127b and between the terminals 127c and 127d of the transformer 103 and N2 denotes the number of turns between the terminals 127e and 127f of the transformer 103.

Next, the operation in the secondary side area 102 of the disarm circuit in this operation is as described in the following 1b-9 to 1b-18.

1b-9: Electromotive force V2n at both ends of each secondary winding increases and exceeds voltage acquired by adding Zener voltage $V_{z28}$ of the Zener diode 128a and the dropout voltage $V_{f29}$ in a forward direction of the Zener diode 129.

$$V2n>V_{z28}+V_{f29} \qquad (7)$$

1b-10: The Zener diode 128 becomes a conducting state.

1b-11: The capacitor 131 is charged (the side of the Zener diode 129 is negative) and the gate capacitance of the semiconductor switch device 133 is charged (the side of the gate is negative) via the resistor 132a.

1b-12: The gate voltage $V_{GE}$ of the semiconductor switch device 133 becomes negative and the switch device is forcedly non-conducting.

1b-13: After the gate voltage $V_{GE}$ of the semiconductor switch device 133 becomes at a level (for example, −15 V) enough to keep the switch device non-conducting (for example, in 2.5 µs.), a control signal N is made to 0 V.

1b-14: The N channel MOSFET 114 becomes a non-conducting state.

1b-15: Back electromotive force which is positive on the side of the terminal 127a and is negative on the side of the terminal 127d is caused on the primary winding of the transformer 103, however, as the terminal 127d at one end of the winding is connected to a power source via the P channel MOSFET 122 and the diode 123 which are respectively in a conducting state, the caused back electromotive force $V1_{rev}$ is inhibited as shown in the following mathematical expression 8.

$$V1_{rev}=(V_{d22}+V_{f23})\times 2 \qquad (8)$$

$V_{ds22}$ denotes the dropout voltage of the P channel MOSFET 122 and $V_{f23}$ denotes the dropout voltage in a forward direction of the diode 123.

1b-16: Electromotive force $V2n_{rev}$ which is positive on the side of the terminal 127e and is negative on the side of the terminal 127f is also generated on the secondary winding by back electromotive force $V1_{rev}$ caused on the primary winding of the transformer 103, however, the level is Zener voltage $V_{z29}$ of the Zener diode 129 or less and the circuit on the secondary side becomes a non-conducting state by the Zener diode 129 (refer to a mathematical expression 9).

$$V2n_{rev}=(V1_{rev}\times N2/N1)<V_{z29} \qquad (9)$$

1b-17: The gate voltage $V_{GE33}$ of the semiconductor switch device 133 increases according to a time constant determined based upon the capacitor 131, the resistor 132 and the gate capacitance of the semiconductor switch device 133.

This time constant is determined so that the gate voltage $V_{GE33}$ of the semiconductor switch device 133 can continue to keep the voltage enough to keep the semiconductor switch device non-conductive for time enough for magnetic energy stored in the core of the transformer 103 to be consumed.

1b-18: Before the gate voltage $V_{GE33}$ of the semiconductor switch device 133 is the threshold 0 V or more and after magnetic energy stored in the core of the transformer 103 is consumed, the level of a control signal N is changed from 0 V to a level at which the N channel MOSFET 114 can be turned on (for example, +5 V).

Afterward, 1b-6 to 1b-18 are repeated.

2. Operation in case the control of the semiconductor switch according to the control signals P, PL, N and NL is disabled (FIG. 2(c)).

In case the control of the semiconductor switch according to the control signals P, PL, N and NL is disabled because of the unexpected cutoff of power supply by the disconnection of a battery and others and the failure of some device such as a single fault of the control circuit, the semiconductor switch is operated by only the secondary side area 102 of the disarm circuit.

Circuit operation in case the four control signals are at the level of 0 V in a state that the semiconductor switch is turned off according to the control signals P, PL, N and NL and electric energy is stored in the electric energy storage section 142 will be described below.

2-0: Electric energy is stored in the electric energy storage section 142 and potential difference between both ends is Vcap. Negative voltage (the side of the resistor for limiting excessive current 140 is negative) is applied to the gate of the semiconductor switch device 133 according to the control signals P, PL, N and NL.

$$V_{GE33}<0 \tag{10}$$

2-1: The control signals P, PL, N and NL become at the level of 0 V.

2-2: The N-channel MOSFET 114, the bipolar transistor 108, the P-channel MOSFET 110, the N-channel MOSFET 126, the bipolar transistor 120 and the P-channel MOSFET 122 are turned off.

2-3: No current flows on the primary winding of the transformer 103.

2-4: Electromotive force caused at both ends of the secondary winding of the transformer 103 gradually decreases and becomes 0 V.

2-5: Accordingly, the gate voltage of the semiconductor switch device 133 gradually rises from a negative level and becomes 0 V.

2-6: Current flows along the following path from the electric energy storage section 142.

The positive terminal of the electric energy storage section 142, the resistor for limiting excessive current 140, the resistor 132, the Zener diode 129, the Zener diode 128, the secondary winding of the transformer 103 (from the terminal 127e to the terminal 127f) and the negative terminal of the electric energy storage section 142.

2-7: Positive voltage determined by Zener voltage Vz28 of the Zener diode 128 and a forward dropout voltage Vf29 of the Zener diode 129 is applied between the gate and the emitter of the semiconductor switch device 133 by the current (a mathematical expression 12).

$$V_{GE33}=V_{z28}+V_{f29} \tag{12}$$

2-8: The gate voltage VGE33 of the semiconductor switch device 133 at this time is larger than the gate threshold voltage VGE(TH) (a mathematical expression 13).

$$V_{GE33}(V_{z28}+V_{f29})>V_{GE(TH)} \tag{13}$$

Therefore, the semiconductor switch device 133 conducts.

2-9: current flows along the following path from the electric energy storage section 142.

The positive terminal of the electric energy storage section 142, the resistor for disarming 141, the semiconductor switch device 133 and the negative terminal of the electric energy storage section 142.

2-10: Energy stored in the electric energy storage section 142 is consumed by the resistor for disarming 141 and voltage Vcap at both ends of the electric energy storage section 142 decreases.

2-11: voltage Vcap at both ends of the electric energy storage section 142 decreases down to a value shown in the following mathematical expression 14.

$$V_{cap}<V_{z28}+V_{f29} \tag{14}$$

2-12: The Zener diode 128 becomes a non-conducting state.

2-13: The gate voltage VGE33 of the semiconductor switch device 133 is lower than the gate threshold voltage VGE(TH) as shown in a mathematical expression 15 and the semiconductor switch device 133 is turned off.

$$V_{GE33}<V_{GE(TH)}$$

The disarm circuit using the semiconductor switch device equivalent to this embodiment uses the semiconductor switch device 133 formed by one stage, however, multistage configuration in which plural semiconductor switch devices are connected in series to increase the withstand voltage can be also adopted. In such a case, the same number of secondary side areas f or respectively directly driving the semiconductor switch devices as the number of the semiconductor switch devices are required.

Examples 1 and 2 of the multistage circuit configuration provided with plural semiconductor switch devices and plural secondary side areas will be concretely described below. The same reference number is allocated to the same part as the part shown in FIG. 1 and the description is omitted.

Multistage Circuit Configuration Example 1

Figure 3:
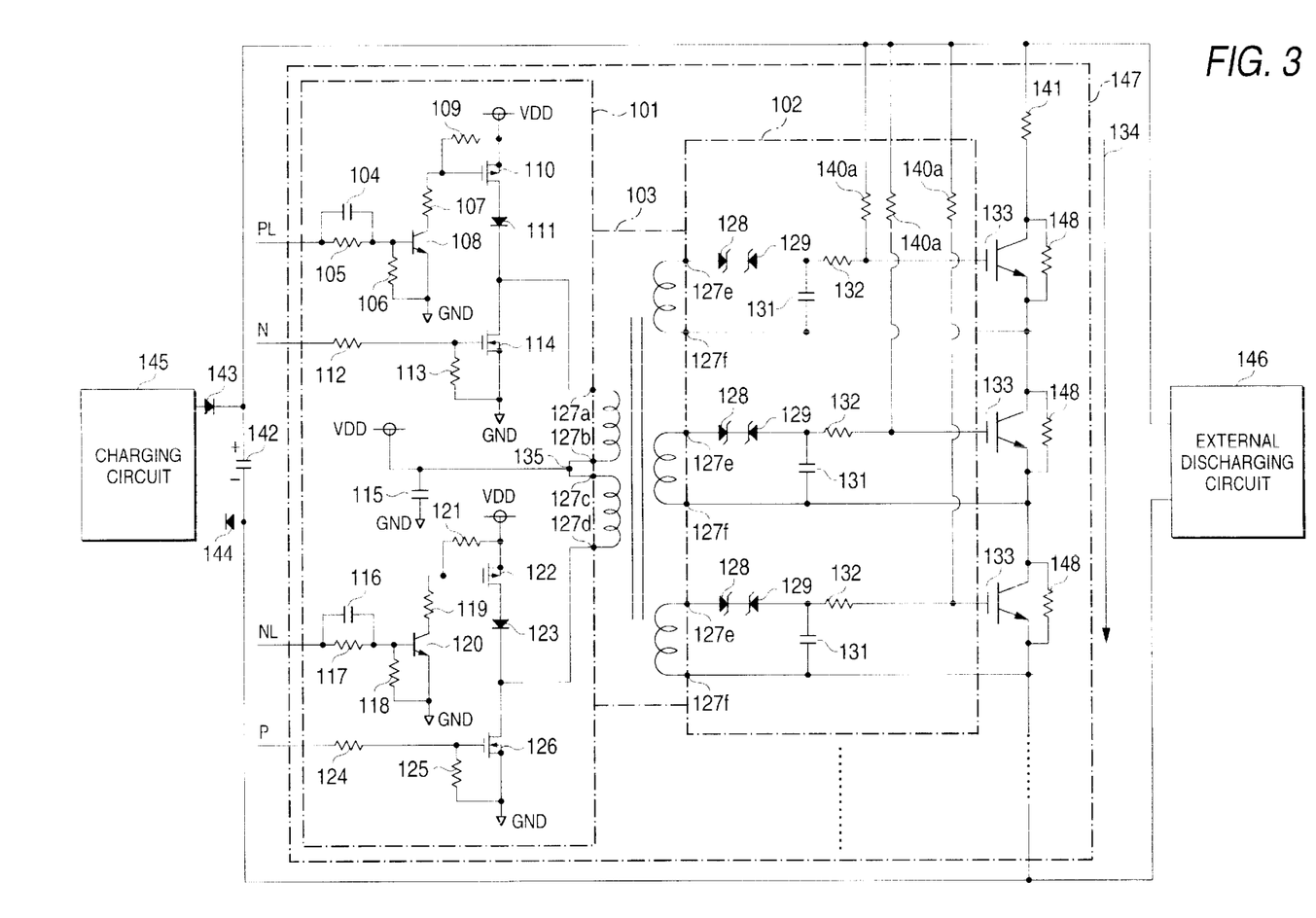
FIG. 3 is a circuit diagram for explaining a multistage circuit configuration example 1 in this embodiment.

FIG. 3 shows a multistage circuit configuration example 1. As shown in FIG. 3, each resistor for limiting excessive current 140a is connected between one terminal (a positive terminal) of an electric energy storage section 142 and a control terminal (the gate) of each semiconductor switch device 133.

It is desirable that a resistor for equalizing the characteristic of each semiconductor switch device 148 is connected between a first terminal (the collector) and a second terminal (the emitter) of each semiconductor switch device 133.

As plural semiconductor switch devices are connected in series in this configuration example, the withstand voltage of the plural semiconductor switch devices against the application of high voltage has a value acquired by adding the withstand voltage of the switch device of each stage, as applied high voltage can be equally distributed to each semiconductor switch device, a semiconductor switch having high withstand voltage can be realized and therefore, a disarm circuit in which high-voltage energy can be disarmed can be provided.

The configuration of the other parts is similar to that of the circuit shown in FIG. 1. The operation is also similar to that of the circuit shown in FIG. 1.

Multistage Circuit Configuration Example 2

Figure 4:
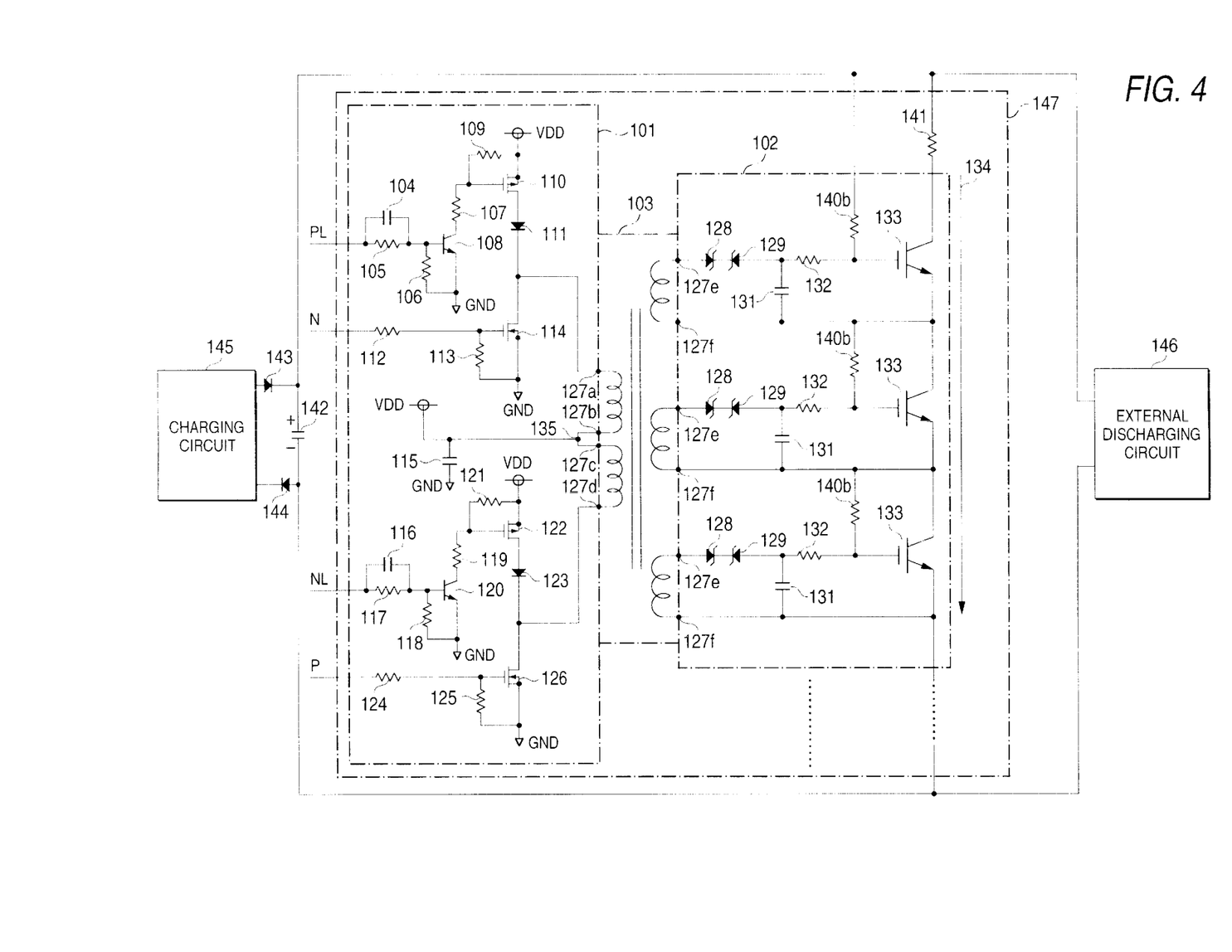
FIG. 4 is a circuit diagram for explaining a multistage circuit configuration example 2 in this embodiment.

FIG. 4 shows the multistage circuit configuration example 2. As shown in FIG. 4, a resistor for limiting excessive current 140b for a first stage is connected between one terminal (a positive terminal) of an electric energy storage section 142 and a control terminal (the gate) of a semiconductor switch device 133 of the first stage, and a resistor for limiting excessive current 140b for a second or the subsequent stage is connected between a second terminal (the emitter) of a semiconductor switch device and a control terminal (the gate) of a semiconductor switch device 133 of the next stage.

As the resistor for limiting excessive current is connected to the control terminal (the gate) of the semiconductor switch device of each stage via a control circuit of the semiconductor switch device of each stage in this configuration example, the withstand voltage of the resistor for limiting excessive current can be distributed by the number of stages, compared with the withstand voltage in case the semiconductor switch device is formed by one stage and in the case of the multistage circuit configuration example 1.

That is, the withstand voltage against the application of high voltage has a value acquired by adding the withstand voltage of the switch device of each stage and applied high voltage can be equally distributed to each semiconductor switch device.

For example, when three stages are provided in case the withstand voltage of 3 kV is required, the withstand voltage of each resistor for limiting excessive current has only to be 1 kV.

The configuration of the other parts is similar to that of the circuit shown in FIG. 1. The operation is also similar to that of the circuit shown in FIG. 1.

The example using an insulated gate bipolar transistor (IGBT) for the semiconductor switch device is described above, however, a MOSFET may be also used for the semiconductor switch device and its circuit configuration example will be described below. The same reference number is allocated to the same part as the part shown in FIG. 1 and the description is omitted.

Circuit configuration example in case of a N-channel MOSFET

Figure 5:
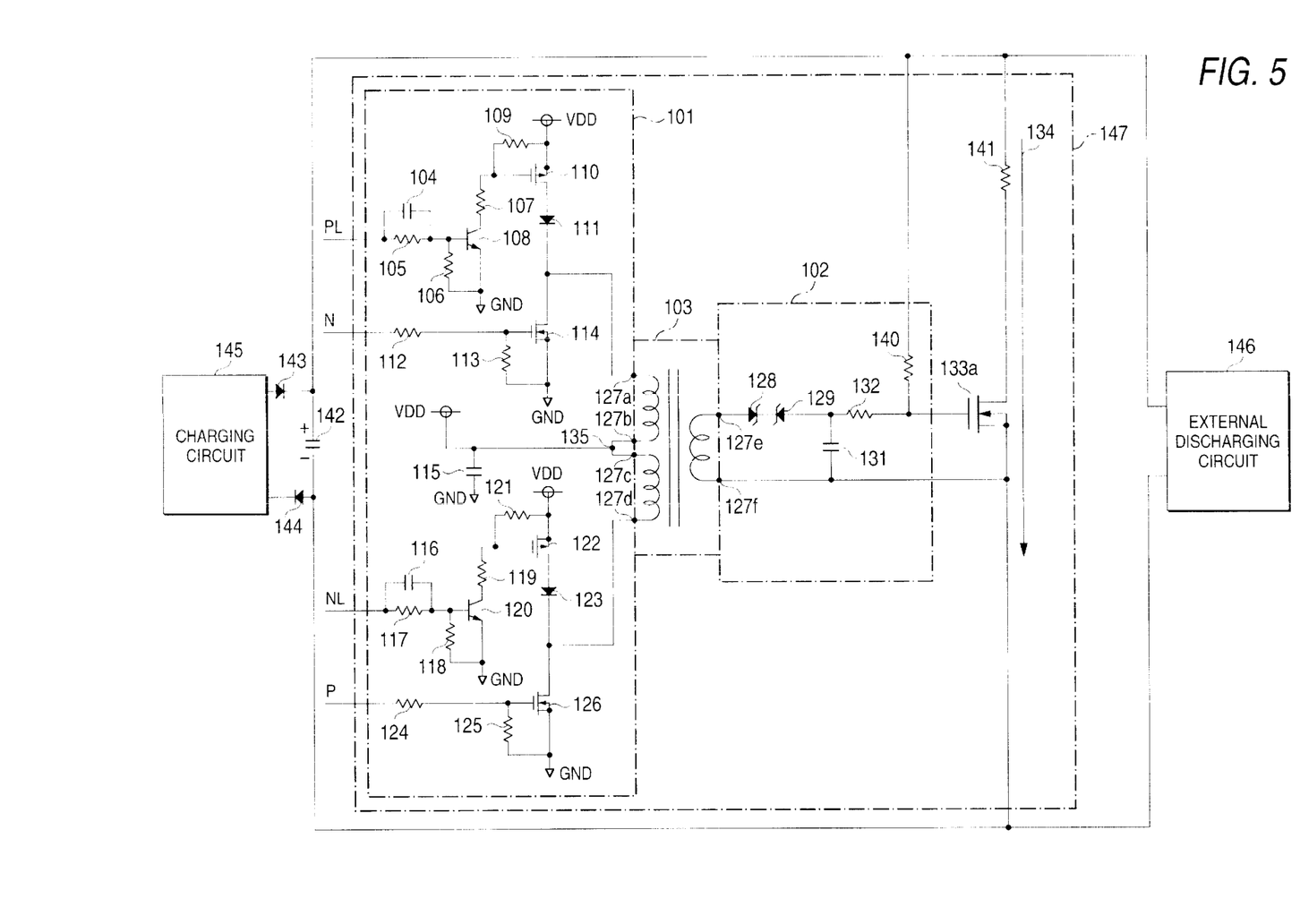
FIG. 5 is a circuit diagram for explaining a circuit configuration example in the case of a N-channel MOSFET in this embodiment.

FIG. 5 shows a configuration example in case a MOSFET is a N-channel MOSFET.

As shown in FIG. 5, a N-channel MOSFET 133a is used for a semiconductor switch device, a first terminal functions as the drain, a second terminal functions as the source, a control terminal functions as the gate, one terminal of an electric energy storage section is a positive terminal.

The configuration of the other parts is similar to that of the circuit shown in FIG. 1. The operation is also similar to that of the circuit shown in FIG. 1.

Circuit Configuration Example in Case of a P-Channel MOSFET

Figure 6:
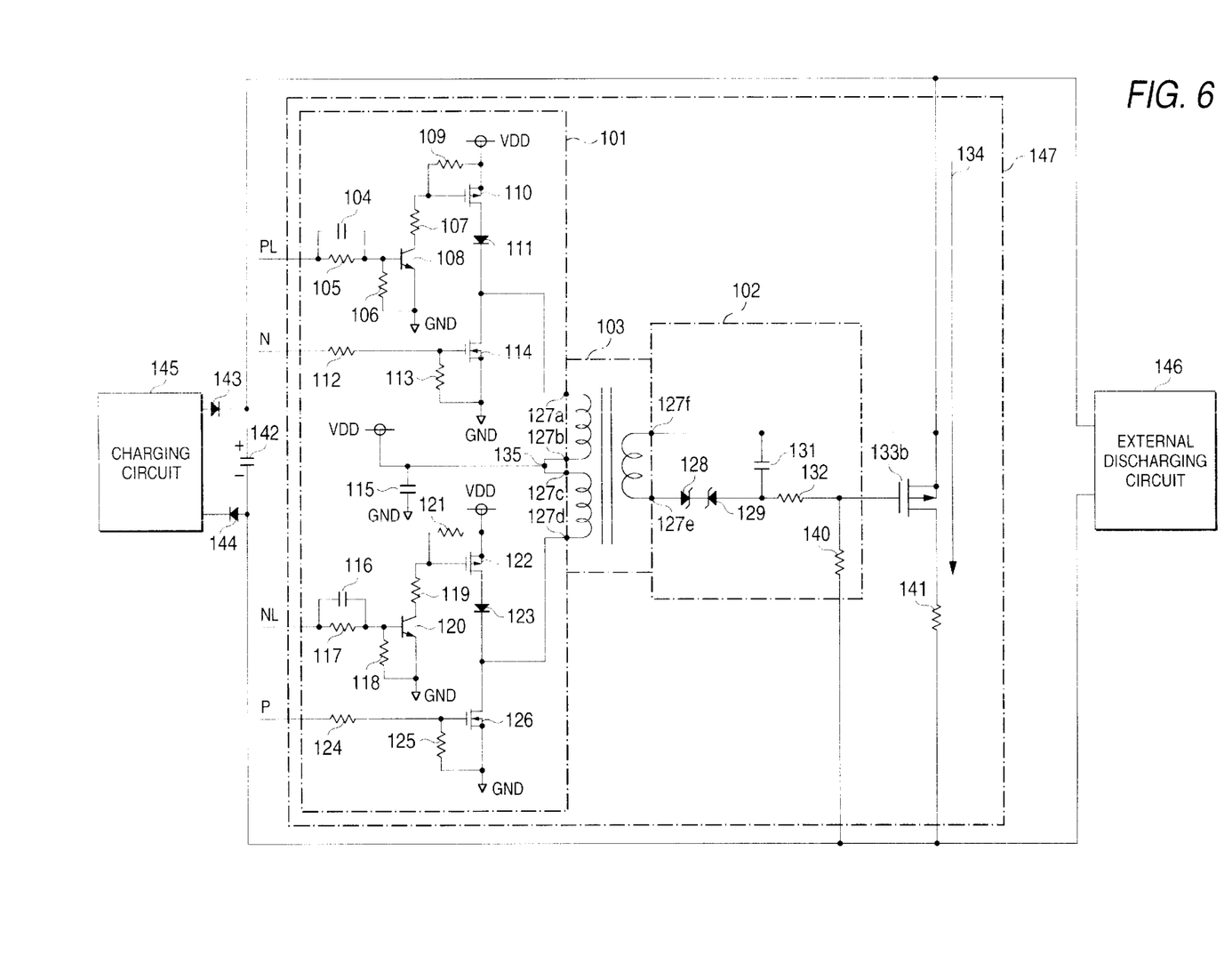
FIG. 6 is a circuit diagram for explaining a circuit configuration example in the case of a P-channel MOSFET in this embodiment.

FIG. 6 shows a configuration example in case a MOSFET is a P-channel MOSFET.

As shown in FIG. 6, a P-channel MOSFET 133b is used for a semiconductor switch device, a first terminal functions as the drain, a second terminal functions as the source, a control terminal functions as the gate and one terminal of an electric energy storage section is a negative terminal.

The configuration of the other part is similar to that of the circuit shown in FIG. 1. The operation is also similar to that of the circuit shown in FIG. 1.

As described in detail above, the disarm circuit using the semiconductor switch device according to a first aspect is based upon a disarm circuit comprising a semiconductor switch device discharging electric energy stored in an electric energy storage section by turning on the semiconductor switch device according to a control signal from a control circuit via a first resistor for disarming the electric energy storage section provided between one terminal of the electric energy storage section and a first terminal of the semiconductor switch device; and a second resistor for limiting current which flows from one terminal of the electric energy storage section and for transmitting the current to a control terminal of the semiconductor switch device, the second resistor being provided between one terminal of the electric energy storage section and the control terminal of the semiconductor switch device.

Hereby, as stored electric energy automatically turns on the semiconductor switch device even if the control of the semiconductor switch is disabled because of the unexpected cutoff of power supply by the disconnection of a battery and others and some failure of an apparatus such as a single fault of the control circuit, electric energy stored in the electric energy storage section can be securely discharged via the resistor for disarming.

According to the disarm circuit using the semiconductor switch device according to a second aspect, the transformer is at least provided, a primary side area controlling current on the primary side of the transformer according to a control signal for controlling the semiconductor switch device, the primary area being provided on the primary side of the transformer;

a secondary side area directly driving the semiconductor switch device, the secondary side area being provided on the secondary side of the transformer, wherein the primary side area receives a control signal, transmits power for controlling the semiconductor switch device to the secondary side area and inhibits back electromotive force caused when current that flows on a primary winding of the transformer is cut off, back electromotive force caused when current flowing in the transformer is cut off is suppressed According to the disarm circuit using the semiconductor switch device according to a third aspect, the secondary side area receives power supplied from the primary side area, transmits power for controlling the semiconductor switch device to the semiconductor switch and cuts off voltage caused by back electromotive force caused when current that flows on a primary winding of the transformer is cut off so that impedance is lower, compared with the second resistor, the control according to a control signal of the semiconductor switch device can be preceded in state in which electric energy is stored in an electric energy storage section.

According to the disarm circuit using the semiconductor switch device according to a fourth aspect, owing to the configuration of the secondary side area, power supplied from the primary side area can be received, power for control can be transmitted to the semiconductor switch device and voltage caused by back electromotive force caused when the primary winding of the transformer is disconnected can be cut off.

According to the disarm circuit using the semiconductor switch device according to a fifth aspect, as the plural semiconductor switch devices are provided, the withstand voltage against the application of high voltage has a value acquired by adding the withstand voltage of the switch device of each stage. Hereby, the disarm circuit wherein higher-voltage energy can be disarmed can be provided.

According to the disarm circuit using the semiconductor switch device according to a sixth aspect, as each second resistor for limiting excessive current is connected between one terminal of the electric energy storage section and the control terminal of each semiconductor switch device, the withstand voltage against the application of high voltage has a value acquired by adding the withstand voltage of the switch device of each stage. Hereby, the disarm circuit wherein higher-voltage energy can be disarmed can be provided.

According to the disarm circuit using the semiconductor switch device according to a seventh aspect, as each third resistor for equalizing the characteristics of each semiconductor switch device is connected between a first terminal and a second terminal of each semiconductor switch device, applied high voltage can be equally distributed to each semiconductor switch device and dispersion among the characteristic of each semiconductor switch device can be eliminated.

According to the disarm circuit using the semiconductor switch device according to an eighth aspect, as the second resistor for limiting excessive current for the first stage is connected between one terminal of the electric energy storage section and the control terminal of the semiconductor switch device on the first stage and another second resistor for limiting excessive current for the second or the subsequent stage is connected between the second terminal of the semiconductor switch device and the control terminal of the semiconductor switch device of the next stage, the withstand voltage against the application of high voltage has a value acquired by adding the withstand voltage of the switch device of each stage, applied high voltage can be equally distributed to each semiconductor switch device and the withstand voltages of the second resistors for limiting current can be distributed.

According to the disarm circuit using the semiconductor switch device according to a ninth aspect, as the insulated gate bipolar transistor (IGBT) is used for the semiconductor switch device, the device (IGBT) having both the low saturation voltage characteristic of a bipolar transistor and the high-speed switching characteristic of a power MOSFET is used. Hereby, the disarm circuit using the semiconductor switch device with little loss and high-speed switching operation can be provided.

According to the disarm circuit using the semiconductor switch device according to a tenth aspect, as a N-channel MOSFET is used for the semiconductor switch device, the first terminal functions as the drain, the second terminal functions as the source, the control terminal functions as the gate and one terminal of the electric energy storage section is a positive terminal, the N-channel MOSFET can be used for the semiconductor switch device.

According to the disarm circuit using the semiconductor switch device according to an eleventh aspect, as a P-channel MOSFET is used for the semiconductor switch device, the first terminal functions as the drain, the second terminal functions as the source, the control terminal functions as the gate and one terminal of the electric energy storage section is a negative terminal, the P-channel MOSFET can be used for the semiconductor switch device.

The electrotherapy apparatus according to a twelfth aspect is provided with the disarm circuit using the semiconductor switch device according to any of the first to the eleventh aspects, the external discharging circuit that generates electric pulse and outputs electric energy to a living body (a patient), the electric energy storage section and the charging circuit that charges the electric energy storage section.

Hereby, the electrotherapy apparatus excellent in safety can be provided wherein even if the semiconductor switch is kept off by the unexpected cutoff of power supply by the disconnection of a battery and others and some failure of the apparatus such as a single fault of the control circuit, electric energy stored in the electric energy storage section can be securely discharged by the resistor for disarming and an operator or a repairman is prevented from getting an electric shock when the electrotherapy apparatus is operated or repaired

What is claimed is:

1. A disarm circuit comprising:
    a semiconductor switch device discharging electric energy stored in an electric energy storage section by turning on the semiconductor switch device according to a control signal from a control circuit via a first resistor for disarming provided between one terminal of the electric energy storage section and a first terminal of the semiconductor switch device; and
    a second resistor for limiting current which flows from one terminal of the electric energy storage section and for transmitting the current to a control terminal of the semiconductor switch device, the second resistor being provided between one terminal of the electric energy storage section and the control terminal of the semiconductor switch device.

2. A disarm circuit using a semiconductor switch device according to claim 1, further comprising:
    at least a transformer;
    a primary side area controlling current on the primary side of the transformer according to a control signal for controlling the semiconductor switch device, the primary area being provided on the primary side of the transformer;
    a secondary side area directly driving the semiconductor switch device, the secondary side area being provided on the secondary side of the transformer,
    wherein the primary side area receives a control signal, transmits power for controlling the semiconductor switch device to the secondary side area and inhibits back electromotive force caused when current that flows on a primary winding of the transformer is cut off.

3. A disarm circuit using a semiconductor switch device according to claim 2, wherein the secondary side area receives power supplied from the primary side area, transmits power for controlling the semiconductor switch device to the semiconductor switch and cuts off voltage caused by back electromotive force caused when current that flows on a primary winding of the transformer is cut off so that impedance is lower, compared with the second resistor.

4. A disarm circuit using a semiconductor switch device according to claim 3 further comprising:
    a first Zener diode connected to a terminal at one end of a secondary winding of the transformer in the secondary side area;
    a second Zener diode one of the two terminals of which is connected in face to face to the same kind terminal of the first Zener diode, the second Zener diode connected to a control terminal of the semiconductor switch device via a resistor, a terminal at the other end of the secondary winding of the transformer is connected to a second terminal of the semiconductor switch device; and
    a capacitor connected between the second Zener diode and the second terminal of the semiconductor switch device.

5. A disarm circuit according to claim 1, wherein a plurality of the semiconductor switch devices are provided.

6. A disarm circuit according to claim 5, wherein the second resistor is respectively connected between one terminal of the electric energy storage section and each control terminal of the plural semiconductor switch devices.

7. A disarm circuit according to claim 6, further comprising:
   a third resistor for equalizing the characteristics of the semiconductor switch devices, eliminating dispersion among the characteristics of respective semiconductor switch devices, the third resistor respectively connected between each first terminal and each second terminal of the plurality of semiconductor switch devices.

8. A disarm circuit according to claim 5, wherein the second resistor for a first stage is connected between one terminal of the electric energy storage section and a control terminal of the semiconductor switch device on the first stage, and another second resistors for limiting excessive current for a second or the subsequent stages are respectively connected between a second terminal of the semiconductor switch device and a control terminal of the semiconductor switch device of the next stage.

9. A disarm circuit using a semiconductor switch device according to claim 1, wherein the semiconductor switch device is an insulated gate bipolar transistor (IGBT), the first terminal functions corresponds to the collector, the second terminal functions corresponds to the emitter, the control terminal functions corresponds to the gate, and one terminal of the electric energy storage section is a positive terminal.

10. A disarm circuit using a semiconductor switch device according to claim 1, the semiconductor switch device is a N-channel MOSFET, the first terminal functions corresponds to the drain, the second terminal functions corresponds to the source, the control terminal functions corresponds to the gate, and one terminal of the electric energy storage section is a positive terminal.

11. A disarm circuit using a semiconductor switch device according to claim 1, wherein the semiconductor switch device is a P-channel MOSFET, the first terminal functions corresponds to the drain, the second terminal functions corresponds to the source, the control terminal functions as the gate, and one terminal of the electric energy storage section is a negative terminal.

12. An electrotherapy apparatus, comprising:
   A disarm circuit including:
      a semiconductor switch device discharging electric energy stored in an electric energy storage section by turning on the semiconductor switch device according to a control signal from a control circuit via a first resistor for disarming the electric energy storage section provided between one terminal of the electric energy storage section and a first terminal of the semiconductor switch device; and
      a second resistor for limiting current which flows from one terminal of the electric energy storage section and for transmitting the current to a control terminal of the semiconductor switch device, the second resistor being provided between one terminal of the electric energy storage section and the control terminal of the semiconductor switch device;
   an external discharging circuit that generates electric stimulation pulse and outputs electric energy to a living body;
   an electric energy storage section; and
   a charging circuit that charges the electric energy storage section.

* * * * *